United States Patent [19]

Leon et al.

[11] 3,966,397
[45] June 29, 1976

[54] DYEING KERATINOUS FIBERS

[75] Inventors: Nicholas Hay Leon, Isleworth; John Alan Swift, Maidenhead, both of England

[73] Assignee: Lever Brothers Company, New York, N.Y.

[22] Filed: June 5, 1973

[21] Appl. No.: 367,282

Related U.S. Application Data

[63] Continuation-in-part of Ser. No. 282,196, Aug. 9, 1972, abandoned, which is a continuation-in-part of Ser. No. 21,498, March 20, 1970, abandoned.

[30] Foreign Application Priority Data

Mar. 28, 1969 United Kingdom.............. 16383/69

[52] U.S. Cl.......................................... 8/10; 8/1 A; 8/10.1; 8/37; 8/41 B; 8/41 R; 8/44; 8/49; 8/54; 8/82; 8/89 R; 8/127.51; 260/160; 260/163; 260/185; 260/191; 260/198; 260/199; 260/200; 424/70; 424/72; 424/226

[51] Int. Cl.²...................... D06P 1/38; D06P 3/10; A61K 7/13

[58] Field of Search .................... 8/37, 36, 10, 10.1, 8/11, 10.2, 1 A, 54, 41 B, 31, 92, 82, 41 R, 44, 49, 89, 127.51; 260/163, 160, 185, 191, 198, 199, 200; 424/70, 72, 226

[56] References Cited
UNITED STATES PATENTS

| | | | |
|---|---|---|---|
| 3,096,141 | 7/1963 | Bennett et al. ...................... | 8/79 X |
| 3,396,736 | 8/1968 | Shansky............................ | 8/10.1 X |
| 3,415,606 | 12/1968 | Randebrock....................... | 8/10.1 |
| 3,567,355 | 3/1971 | Boosen et al. ...................... | 8/10.1 |

OTHER PUBLICATIONS

"On Carboxymethyl Dithiophenylacetate and its Reactions with Amines, Amino Acids and Peptides", A. Kjaer, Acta Chem. Scand., vol. 6, pp. 327-332 (1952).
"Keratin Substantivity", R. L. Goldemberg, Drug and Cosmetic Industry, vol. 85, No. 5, pp. 618-619, 694-696 (1959).

*Primary Examiner*—Benjamin R. Padgett
*Assistant Examiner*—T. S. Gron
*Attorney, Agent, or Firm*—Arnold Grant

[57] ABSTRACT

A process for dyeing keratinous fibers such as hair which comprises reacting the hair with a dyestuff of the general formula

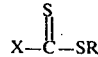

where X is a chromophoric group, such as a group formed by coupling a phenylene diazonium salt with a diazo coupling compound, and where R has the formula $-R'COOH$, $-R'COOCH_3$, $-CH_2CH_2OH$ or $-CH_3$ in which R' is an alkylene group containing 1,2 or 3 carbon atoms. The process gives good coloring of hair without damaging the condition.

The invention also relates to novel dyes for use in the process and to processes for their production, and to dyeing compositions containing the dyes.

9 Claims, No Drawings

DYEING KERATINOUS FIBERS

This application is a continuation-in-part of Ser. No. 282,196, filed Aug. 9, 1972 now abandoned, which is a continuation-in-part of Ser. No. 21,498, filed Mar. 20, 1970 now abandoned.

This invention relates to a process for dyeing keratinous fibres and to compositions for use in such a process. The invention also concerns novel dyes for dyeing the fibres and to processes for the production of such dyes.

According to the invention there is provided a process for dyeing keratinous fibres which comprises reacting the keratinous fibres with a dyestuff of the general formula

  (I)

where X is a chromophoric group and where R has the formula
-R'COOH
-R'COOCH$_3$
-CH$_2$CH$_2$OH
or -CH$_3$
in which R' is an alkylene group containing 1,2 or 3 carbon atoms.

In a second aspect of the invention there is provided a keratinous fibre-reactive dyestuff of the general formula I where X and R are as defined above.

Further the invention comprises a composition for dyeing keratinous fibres comprising an aqueous solution of the keratinous fibre-reactive dyestuff as defined above together with a surface active agent and/or a thickening agent.

The invention also includes a process for preparing a dyestuff having the general formula

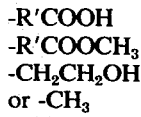  (II)

where
R is as defined above,
R$^2$ is the residue of a diazo coupling compound,
Y is a phenylene or substituted phenylene group, and
n is 1 or 2, which process comprises reacting a diazonium salt of the general formula

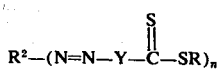

where Z is a cation, with a diazo coupling compound.

In a final aspect the invention provides a process for preparing a diazonium salt as defined above which comprises
a. treating a compound of the general formula
AcHN-Y-CHO
where
Ac is an acyl group and
Y is as defined above with a mixture of piperidine and sulphur to form a compound of the general formula

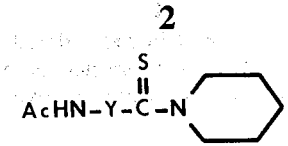

b. hydrolysing this compound to remove the acyl group,
c. treating the resulting compound with an α-bromocarboxylic acid or ester of the formula BrR'COOH or BrR'COOCH$_3$ where R' is as defined above to form a compound of the general formula

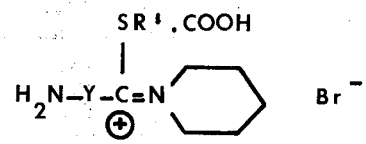

d. treating this compound with hydrogen sulphide to form a carboxy-alkyl carbodithioate compound of the general formula

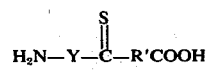

and optionally
e. treating the carboxy-alkyl carbodithioate compound with a thiol of the formula HSCH$_2$CH$_2$OH to form a compound of the general formula

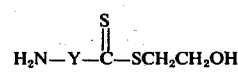

or
f. treating the carboxy-alkyl carbodithioate compound with a thiol of the formula HSCH$_3$ to form a compound of the general formula

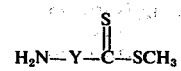

and
g. diazotizing the resulting amine to form a diazonium salt.

In a preferred embodiment of the process of dyeing keratinous fibres the fibres are, before reaction with the dyestuff, pre-treated with a reducing agent capable of reducing the S-S bridges in the keratin of the fibres to —SH groups. This preferred method results in much more intense colours being obtained. In another way of performing the dyeing process the keratinous fibres are treated with a reducing agent simultaneously with the reaction with the dyestuff. Preferably the reducing agent used is a thioglycolate that is thioglycolic acid or a salt therefore or a mercaptan.

The pH of the aqueous dyeing medium is desirably of from 4 to 12, preferably 8 to 10.

The colours produced by the dyeing process are fast because reactive dyeing takes place. A further advantage is that, as described in more detail below, only mild conditions of treatment are necessary.

The preferred keratinous fibre-reactive dyestuff has the general formula

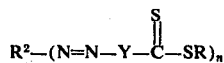

where
R is as defined above,
R² is the residue of a diazo coupling compound,
Y is a phenylene or substituted phenylene group, and
n is 1 or 2.

Examples of keratinous fibre-reactive dyestuffs within the scope of the invention are indicated below in Table 1.

Table 1

| Diazo Coupling Compound (R²H) | R | Dyestuff No | Shade |
|---|---|---|---|
| 1-naphthol-4-sulphonic acid | CH₂COOH | 1 | Red |
| 4-chloro-3-(3-methyl-5-oxo-2-pyrazolin-1-yl)benzene sulphonic acid | CH₂COOH | 2 | Yellow |
|  | CH₂CH₂OH | 2A | Yellow |
| 2,5-dichloro-4-(3-methyl-5-oxo-2-pyrazolin-1-yl)-benzenesulphonic acid | CH₂COOH | 3 | Yellow |
| 7-amino-1-naphthol-3-sulphonic acid | CH₂COOH | 4 | Reddish Vi. |
|  | CH₂CH₂OH | 4A | Reddish Vi. |
| 6-amino-1-naphthol-3-sulphonic acid | CH₂COOH | 5 | Red |
|  | CH₂CH₂OH | 5A | Red |
| 7-acetamido-1-naphthol-3-sulphonic acid | CH₂COOH | 6 | Red |
| 8-amino-1-naphthol-7-phenyl-azo-3,6-disulphonic acid | CH₂COOH | 7 | Violet |
|  | CH₂CH₂OH | 7A | Violet |
|  | CH₃ | 7B | Violet |
| 8-amino-1-naphthol-7-(4-dimethylamino-phenylazo)-3,6-disulphonic acid | CH₂COOH | 8 | Violet |
| 6-amino-1-naphthol-5-(4-dimethylaminophenylazo)-3-sulphonic acid | CH₂COOH | 9 | Brownish Red |
|  | CH₂CH₂OH |  |  |
| 8-amino-1-naphthol-7-(4-dimethylaminophenylazo)-5-sulphonic acid | CH₂COOH | 10 | Blueish Grey |
|  | CH₂CH₂OH | 10A |  |
| 8-amino-1-naphthol-7-(4-acetamidophenylazo)-3,6-disulphonic acid | CH₂COOH | 11 | Violet |
| 8-amino-1-naphthol-7-(4-acetamidophenylazo)-5-sulphonic acid | CH₂COOH | 12 | Blue |
| 7-methylamino-1-naphthol-3-sulphonic acid | CH₂COOH | 13 | Brown |
| 8-acetamido-1-naphthol-3,6-disulphonic acid | CH₂COOH | 14 | Red |

As implied above, the above diazo dyestuffs were prepared by diazotising the amine of formula

and reacting the resulting diazonium salts with a diazo coupling compound in alkaline solution.

The following examples illustrate the preparation of four amines of the above general formula, in which R is —CH₂.COOH, —CH₂CH₂OH, —CH₃ and —CH₂COOCH₃.

EXAMPLE 1

1-(4-Acetamidothiobenzoyl)piperidine

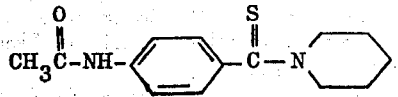

4-Acetamidobenzaldehyde (81.8 g, 0.5 mole), piperidine (42.6 g, 0.5 mole), sulphur (16.0 g, 0.5 mole) and pyridine (85 ml) were mixed together and refluxed for 4 hours with stirring. After coling to room temperature, water (50 ml) was added and the reaction mixture was acidified with concentrated hydrochloric acid in the cold. The crystalline solid which formed was filtered off, washed with water and dried in vacuo at a temperature of under 50°C. Recrystalisation of the crude product (120 g) from ethanol gave pale yellow crystals (108 g; 82.4%), m.p. 202°-203°.

1-(4-Aminothiobenzoyl)piperidine

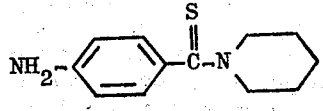

1-(4-Acetamidothiobenzoyl)piperidine (131.2 g, 0.5 mole), ethanol (500 ml), water (1 l) and concentrated sulphuric acid (125 ml) were mixed together and refluxed for 16 hours with stirring; nearly all the solid dissolved during the first hour. The reaction mixture was cooled to about 40°C and filtered quickly to remove any insoluble material. The filtrate was then made alkaline with 6N sodium hydroxide solution using external ice-cooling. The yellow crystalline solid was filtered off, washed with water and dried in vacuo at a temperature of under 50°C. Recrystallisation of the crude product (91 g; m.p. 162°–164°) by dissolving in 6 volumes of warm chloroform (about 546 ml) followed by adding 5 volumes of petroleum ether (b.p. 40°–60°) (about 455 ml) yielded yellow crystals (85 g; 77.3%), m.p. 164°–165°.

Carboxymethyl 4-Aminobenzenecarbodithioate

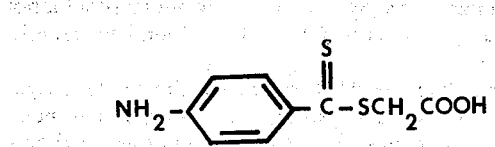

A warm solution of bromoacetic acid (41.7 g, 0.3 mole) in dry 1,2-dichloroethane (about 85 ml) was added to a warm solution of 1-(4-aminothiobenzoyl)-piperidine (66.0 g, 0.3 mole) in 12 volumes of dry 1,2-dichloroethane (about 792 ml). After 16 hours at room temperature, the gummy S-carboxymethyl-(4-aminothiobenzoyl)piperidinium bromide was separated by decanting the supernatant liquid, washed quickly with a small amount of dry ether and used immediately in the next reaction.

Absolute ethanol (ca 540 ml) was added to the above gummy material in the same flask, and a slow steam of dry hydrogen sulphide gas was passed into the stirred mixture under anhydrous conditions. When the reaction mixture became homogenous (about 1–2 hours), hydrogen sulphide gas was passed through the reaction mixture for a further 2–3 hours with external ice-cooling. After storage for 16 hours at 0°–5°C, the reaction mixture was poured into 3 volumes of ice-water with stirring. The yellow powdery precipitate was filtered off, washed with water and dried in vacuo at a temperature of under 50°C. One crystallisation of the crude product (m.p. 120°–121°; 62.4 g or 87.2% based on 1-(4-aminothiobenzoyl)piperidine) by dissolving in 5 volumes of warm methanol followed by adding 5 volumes of warm water furnished the pure product, m.p. 130°–131.5°(55.8 g; 81.9% based on 1-(4-aminothiobenzoyl)-piperidine).

EXAMPLE 2

2-Hydroxyethyl 4-Aminobenzenecarbodithioate

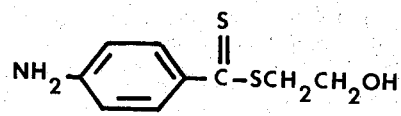

Crude carboxymethyl 4-aminobenzenecarbodithioate (7.48 g, 0.033 mole) was dissolved in 0.5 N (66 ml) sodium hydroxide solution containing 10% by weight of sodium bicarbonate and the solution was filtered to remove traces of insoluble material. 2-Mercaptoethanol (2.9 g, 0.037 mole) was added to the stirred filtrate and the reaction mixture soon became turbid as the product began to separate out. After standing for 1 hour at room temperature, the orange precipitate was filtered off, washed with water, and dried in vacuo at a temperature of below 50°C. The yield of the product, an orange crystalline powder, m.p. 87.5°–89.5° was 6.13 g or 87%.

EXAMPLE 3

Methyl 4-Aminobenzenecarbodithioate

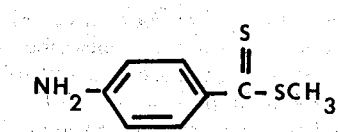

Methyl mercaptan was passed into a filtered solution of crude carboxymethyl 4-aminobenzenecarbodithioate (7.48 g, 0.033 mol) in 66 ml of 0.5 N of sodium hydroxide solution containing 10% by weight sodium bicarbonate under external ice-cooling for about 10 minutes. A yellow precipitate separated out gradually as the colour of the aqueous solution was discharged. After standing for 1 hour at 0°–5°C, the precipitate was filtered off, washed with 10% by weight sodium bicarbonate solution, then with water and dried in vacuo at a temperature of below 50°C. The yield of the yellow crystalline powder, m.p. 74.5°–75.5° (decomp.) was 5.3 g or 87.7%.

EXAMPLE 4

Methyl Ester of S-Carboxymethyl-(4-aminothiobenzoyl)piperidinium Bromide

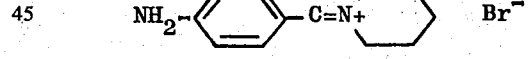

A solution of methyl bromoacetate (23.0 g, 0.15 mole) in dry 1,2-dichloroethane (230 ml) was added to a warm solution of 1-(4-aminothiobenzoyl)piperidine (33.0 g, 0.15 mole) in volumes of dry 1,2-dichloroethane (ca. 396 ml). After storage for 2–3 days, the yellow crystalline solid was filtered off, washed with dry ether and dried in a vacuum desiccator over phosphorus pentoxide to give the bromide (56 g; quantitative yield) as yellow crystals, m.p. 156°–160° (decomp.). The crude product was sufficiently pure and was used immediately in the next reaction.

Methyl Ester of Carboxymethyl 4-Aminobenzenecarbodithioate

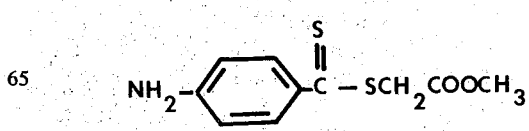

A slow steam of dry hydrogen sulphide gas was passed for 2–3 hours through a stirred suspension of the methyl ester of S-carboxymethyl-(4-aminothiobenzoyl)piperidinium bromide (56 g, 0.15 mole) in absolute ethanol (500 ml) using external ice-cooling. The reaction mixture soon became red and homogeneous. After overnight storage at 0°–5°C, the reaction mixture was poured into 5-volumes of ice-water and the crystalline precipitate was filtered off, washed with water and dried in vacuo at a temperature of below 50°C. The yield of the product, yellow crystals, m.p. 89°–90°, was 29.5 g or 81.5%.

A general method for the preparation of an azo dye in accordance with the invention is described in the following examples. Example 5 describes a general procedure for preparing a diazonium salt solution, Example 6 a procedure for preparing a solution or suspension of a coupling compound and Example 7 a procedure for performing the diazo coupling reaction. It will be appreciated that the structure of the resultant dyestuff can be varied by varying the nature and relative proportion of the amine and the diazo coupling compound.

EXAMPLE 5

Diazonium salt solution

An amine of the general formula

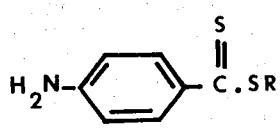

(0.1 mole) is dissolved in 10 volumes of 80% acetic acid by warming to about 45°C on a water-bath. To the above stirred solution concentrated hydrochloric acid (27 ml, 0.3 mole) is added and the resulting suspension is diazotized with a solution of pure sodium nitrite (6.90 g, 0.10 mole) in water (35 ml) at 0°–5°C. The amine hydrochloride dissolves to give a clear dark-red solution. After 15 minutes, any excess nitrite present is destroyed by the addition of urea.

EXAMPLE 6

Coupling Compound Solution (or suspension)

A minimum amount of 2 N sodium hydroxide solution is added to a suspension of a coupling compound, for example N-acetyl gamma acid (0.1 mole) in water (100 ml) to effect solution. The solution is then cooled to 5°C, stirred vigorously and acidified with 2N hydrochloric acid solution to pH 4.

EXAMPLE 7

Diazo Coupling

The diazonium salt solution prepared in Example 5 is poured into the coupling compound solution prepared as in Example 6 at 0-5°C with stirring. After the addition, the pH of the reaction mixture is adjusted to about 5 with concentrated sodium hydroxide solution. After stirring the reaction mixture at room temperature for an hour the dye is precipitated completely by the addition of solid sodium chloride (15%, w/v) to the stirred suspension and the pH of the mixture is adjusted to 5. The dye is filtered off, washed with 10% sodium chloride solution and dried in vacuo below 50°C.

As indicated above it has been discovered that more intense shades are obtainable if the hair is treated to provide more sulphydryl groups by reducing the disulphide bridges of the keratin to sulphydryl groups. The reduction may either be effected before the treatment of the fibre with the reactive dyes of the invention or it may be effected simultaneously with the dyeing treatment. From the point of view of convenience to the user it is preferable that reduction should be effected simultaneously with dyeing so that treatment is a one stage process. Thioglycollic acid and mercaptoethanol are reducing agents which we have found to be suitable.

In some cases, particularly where the reactive dyestuff is only sparingly soluble in water, it has been found advantageous to add small quantities of detergent to the dyeing solutions as a solubiliser for the dyestuff.

The addition of an organic solvent, for example an aliphatic alcohol, in particular ethanol, can help to improve the match between the dyeing solution and the dyed hair.

The following example illustrates the use of a fibrereactive dyestuff in a process of dyeing hair in accordance with the invention.

EXAMPLE 8

A switch of virgin blonde Italian Blue String hair was immersed in a dyeing solution (liquor to hair ratio 2:1) for 20 minutes at 35°C. The dyeing solution was gently agitated periodically.

The dyeing solution had the following composition

| | % by weight |
|---|---|
| 2-Mercaptoethanol | 5 |
| Dyestuff No 4 (Table 1) | 5 |
| Nonionic surface-active agent | 1 |
| Water | balance to 100 |

The solution was adjusted to pH 9 with sodium hydroxide solution.

After removal from the dyeing solution and washing in running water, the hair switch was seen to be dyed to an intense reddish violet shade.

The wash fastness to shampoo of hair dyed with the above dyeing solution is comparable to that of commercial permanent oxidation hair colourants.

The following example illustrates a process in accordance with the invention in which, prior to the dyeing step the hair is reduced with ammonium thioglycollate.

EXAMPLE 9

A switch of virgin blonde Italian Blue String hair was reduced using a dilute commercial permanent waving solution containing 2.0% by weight of thioglycollic acid for 20 minutes. The switch was then washed.

It was then dyed using the procedure of the previous example with a dyeing solution having the following composition.

| | % by weight |
|---|---|
| Dyestuff No 2 (Table 1) | 2.00 |
| Sodium lauryl sulphate | 0.01 |
| Acrylic thickener | 0.1 |
| Phosphate buffer solution | balance to 100 |
| Water | |

The pH of the dyeing solution was buffered at pH 6.4. The hair switch was dyed to a golden yellow shade.

No noticeable colour fading of any of the hair switches dyed with the reactive dyes of the invention was observed, even though they were exposed to bright sunlight in the laboratory.

As regards the physical properties of the dyed hair switches, comparison of dyed and undyed fibres at 100% and ambient relative humidity reveals no significant difference in the load/extension behaviour in the 5–20% stretch region. However, at high humidity, loads that produce extensions of more than 20% in undyed fibres will cause greater extensions in dyed fibres although this weakening under high load and humidity is not disadvantageous in practice. In general, hair condition of the dyed switches was maintained satisfactorily.

What is claimed is:

1. A process for dyeing hair which comprises contacting the hair with a dyestuff, the dyestuff being solubilised in an aqueous or alcoholic medium and being of the formula

wherein
R is selected from the group consisting of
- R'COOH
- R'COOCH$_3$
- CH$_2$CH$_2$OH
and,
- CH$_3$
in which R' is an alkylene group containing 1, 2 or 3 carbon atoms,
R$^2$ is the residue of a diazo coupling compound,
Y is a phenylene or substituted phenylene group and
n is 1 or 2.

2. A process for dyeing hair according to claim 1 wherein prior to or simultaneously with contacting the hair with the dyestuff, the hair is treated with a reducing agent capable of reducing the S-S bridges in the keratin of the hair to -SH groups.

3. A process as claimed in claim 2 wherein the reducing agent is a thioglycollate.

4. A process as claimed in claim 2, wherein the reducing agent is thioglycollic acid.

5. A process as claimed in claim 2 wherein the reducing agent is a mercaptan.

6. A process according to claim 1 wherein the aqueous or alcoholic medium is at a pH of from about 4 to about 12.

7. A process according to claim 6 wherein the pH is from about 4 to about 10.

8. A composition for dyeing hair comprising an aqueous solution of a surface active agent and a dyestuff having the formula

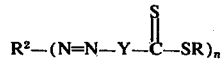

wherein
R is selected from the group consisting of
- R'COOH
- R'COOCH$_3$
- CH$_2$CH$_2$OH
and,
- CH$_3$
in which R' is an alkylene group containing 1, 2 or 3 carbon atoms,
R$^2$ is the residue of a diazo coupling compound
Y is a phenylene or substituted phenylene group and
n is 1 or 2.

9. A composition for dyeing hair comprising an aqueous solution of a thickening agent and a dyestuff having the formula

where
R is selected from the group consisting of
- R'COOH
- R'COOCH$_3$
- CH$_2$CH$_2$OH
and
- CH$_3$
in which R' is an alkylene group containing 1, 2 or 3 carbon atoms,
R$^2$ is the residue of a diazo coupling compound
Y is a phenylene or substituted phenylene group and
n is 1 or 2.

* * * * *